United States Patent [19]

Schubart et al.

[11] 4,329,477

[45] May 11, 1982

[54] PROCESS FOR THE PRODUCTION OF 4- OR 5-METHYL-2-MERCAPTOBENZIMIDAZOLE

[75] Inventors: Rüdiger Schubart, Bergisch-Gladbach; Günter P. Langner, Leverkusen, both of Fed. Rep. of Germany

[73] Assignee: Bayer AG, Leverkusen, Fed. Rep. of Germany

[21] Appl. No.: 237,864

[22] Filed: Feb. 25, 1981

[30] Foreign Application Priority Data

Mar. 4, 1980 [DE] Fed. Rep. of Germany ....... 3008159

[51] Int. Cl.$^3$ ............................................ C07D 487/00
[52] U.S. Cl. ................................................... 548/305
[58] Field of Search .................. 548/305; 568/20, 61, 568/67, 69; 564/26

[56] References Cited

U.S. PATENT DOCUMENTS 3,895,025 7/1975 Goodman ............................ 548/305
4,172,833 10/1979 Whitney et al. .................... 548/305

*Primary Examiner*—Jane T. Fan
*Attorney, Agent, or Firm*—Connolly and Hutz

[57] ABSTRACT

A process for the production of 4- or 5-methyl-2-mercaptobenzimidazole, characterized in that 1 part of 4- or 5-methyl benzimidazolone is reacted with 3 to 10 parts by weight of carbon disulphide in the presence of 1% to 12% by weight of a basic catalyst, based on benzimidazolone, at a temperature in the range from 200° C. to 300° C. 4- or 5-methyl-2-mercaptobenzimidazole is used in the rubber industry as an anti-ager for both natural and synthetic rubber either on its own or in combination with other standard anti-agers.

6 Claims, No Drawings

PROCESS FOR THE PRODUCTION OF 4- OR 5-METHYL-2-MERCAPTOBENZIMIDAZOLE

This invention relates to a process for the production of 4- or 5-methyl-2-mercaptobenzimidazole by reacting a corresponding benzimidazolone with carbon disulphide.

4- or 5-methyl-2-mercaptobenzimidazole is used in the rubber industry as an anti-ager for both natural and synthetic rubber either on its own or in combination with other standard anti-agers. As can be seen, for example, from German Pat. No. 557,138, the compounds may be obtained by reacting a diaminotoluene with carbon disulphide.

The object of the present invention is to provide another process.

Accordingly, the present invention provides a process for the production of 4- or 5-methyl-2-mercaptobenzimidazole which is characterized in that 1 part by weight of 4- or 5-methyl benzimidazolone is reacted with 3 to 10 parts by weight of carbon disulphide in the presence of from 1% to 12% by weight of a basic catalyst, based on the benzimidazolone, at a temperature in the range from 200° C. to 300° C.

The reaction is preferably carried out over a period of from 3 to 10 hours and, with particular preference, over a period of from 4.5 to 7 hours. The preferred temperature range is from 240° C. to 260° C. Carbon disulphide is preferably added in 4 to 6 parts by weight per part of the benzimidazolone whilst the basic catalyst is preferably added in a quantity of from 5 to 10% by weight.

Pressure builds up during the reaction and provision has to be made to ensure that this pressure is maintained and does not escape from the apparatus.

The basic catalyst used is preferably an alkali metal or alkaline earth metal carbonate or hydroxide, for example sodium, potassium, lithium or calcium carbonate or sodium or potassium hydroxide.

4- or 5-methyl benzimidazolone is known. It is possible to produce this starting material from a waste product accumulating in large quantities in isocyanate chemistry. Thus, DE-OS No. 2,703,313 describes a process by which the residue accumulating in the distillation of tolylene diisocyanate may be split by means of ammonia into diaminotoluene and 4- or 5-methyl benzimidazolone. The benzimidazolone may readily be isolated from this mixture. The resulting mixture of 4- or 5-methyl benzimidazolone may be converted by the process according to this invention into a mixture of 4- and 5-methyl-2-mercaptobenzimidazole which is eminently suitable for use as an anit-ager for rubbers.

The process according to a particular embodiment of the invention may be carried out as follows:

50 g of 4- or 5-methyl benzimidazolone are stirred for 5 hours at 250° C. with 250 g of carbon disulphide and 5 g of potash. The reaction vessel is then vented and excess carbon disulphide is removed, the residue is dissolved in dilute sodium hydroxide solution and the resulting solution is clarified with A-carbon, the filtrate is acidified with hydrochloric acid and the deposit is filtered off under suction. The deposit is washed with water and dried in vacuo, leaving 51.5 g of a product mixture melting at 283° C. to 289° C. which, according to its IR-spectrum, is identical with a sample obtained by reacting 3- or 4-methyl-1,2-diaminobenzene with carbon disulphide.

We claim:

1. A process for the production of 4- or 5-methyl-2-mercaptobenzimidazole, wherein 1 part of 4- or 5-methyl benzimidazolone is reacted with 3 to 10 parts by weight of carbon disulphide in the presence of 1% to 12% by weight of basic catalyst, based on benzimidazole, at a temperature in the range from 200° C. to 300° C.

2. A process as claimed in claim 1, wherein 1 part by weight of 4- or 5-methyl benzimidazolone is reacted with 4 to 6 parts by weight of carbon disulphide.

3. A process as claimed in claim 1, wherein the reaction is carried out in the presence of from 5% to 10% by weight of the basic catalyst.

4. A process as claimed in claim 1, wherein the reaction is carried out at a temperature in the range from 240° C. to 260° C.

5. A process as claimed in claim 1, wherein an alkali metal and/or alkaline earth metal carbonate and/or hydroxide is used as the basic catalyst.

6. A process as claimed in claim 5 wherein potash or potassium hydroxide is used as the basic catalyst.

* * * * *